United States Patent

McBrien et al.

Patent Number: 5,100,384
Date of Patent: Mar. 31, 1992

[54] METHOD AND DEVICE FOR PERCUTANEOUS INTUBATION

[75] Inventors: P. Bruce McBrien; John A. Karpiel, both of Winston-Salem, N.C.

[73] Assignee: Wilson-Cook Medical, Inc., Winston-Salem, N.C.

[21] Appl. No.: 503,454

[22] Filed: Mar. 30, 1990

[51] Int. Cl.⁵ ............................................. A01M 29/00
[52] U.S. Cl. .................................. 604/99; 604/175
[58] Field of Search ............... 604/158, 160, 93–103, 604/174, 175, 178, 280

[56] References Cited

U.S. PATENT DOCUMENTS

| | | |
|---|---|---|
| 3,640,282 | 8/1972 | Kamen et al. |
| 3,799,173 | 3/1974 | Kamen .................. 604/96 x |
| 4,573,576 | 3/1986 | Krol .................... 206/471 |
| 4,581,017 | 4/1986 | Sahota .................. 604/101 |
| 4,668,225 | 5/1987 | Russo et al. ............ 604/270 |
| 4,795,430 | 1/1989 | Quinn et al. ............ 604/97 |
| 4,834,712 | 5/1989 | Quinn et al. ............ 604/175 |
| 4,906,233 | 3/1990 | Moriuchi et al. ......... 604/174 |
| 4,921,479 | 5/1990 | Gray et al. ............. 604/53 |
| 4,981,471 | 1/1991 | Quinn et al. ............ 604/97 |

Primary Examiner—John D. Yasko
Assistant Examiner—Adam Cermak
Attorney, Agent, or Firm—Richard J. Godlewski

[57] ABSTRACT

A catheter for intubating a stoma formed by a percutaneous endoscopic technique includes a multi-lumen tube and an inflatable cuff for retaining the catheter in place. The tube includes a fluid lumen for conveying fluid into a patient and an inflation lumen having a port in communication with the interior of the cuff to allow for the egress and ingress of fluid to the cuff. The cuff has contained therein a resilient sponge-like material which has the property that it will remain in its compressed state for an ascertainable period of time after having been maintained in the compressed state for a predetermined period of time, e.g., at least 24 hours. A period of time, not less than the predetermined period of time, prior to the intubation procedure, the cuff is compressed to expel air from the cuff through the inflation lumen and to compress the sponge-like material inside the cuff. A tubular sleeve is applied to the outside of the cuff to maintain the cuff and sponge-like material in its collapsed state. Prior to the intubation procedure, the sleeve is removed. Upon completion of intubation, when the cuff is positioned in a cavity, such as the stomach, internal to the patient, the sponge-like material is expanded by injecting a liquid such as distilled water into the cuff via the inflation lumen. The inflation lumen is then closed.

15 Claims, 2 Drawing Sheets

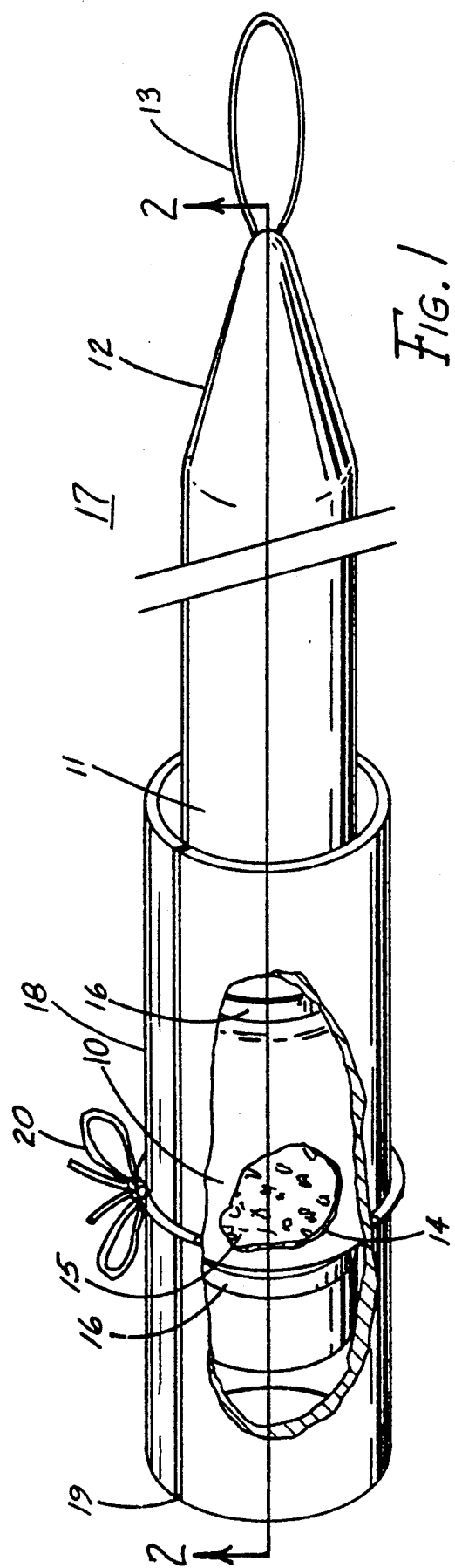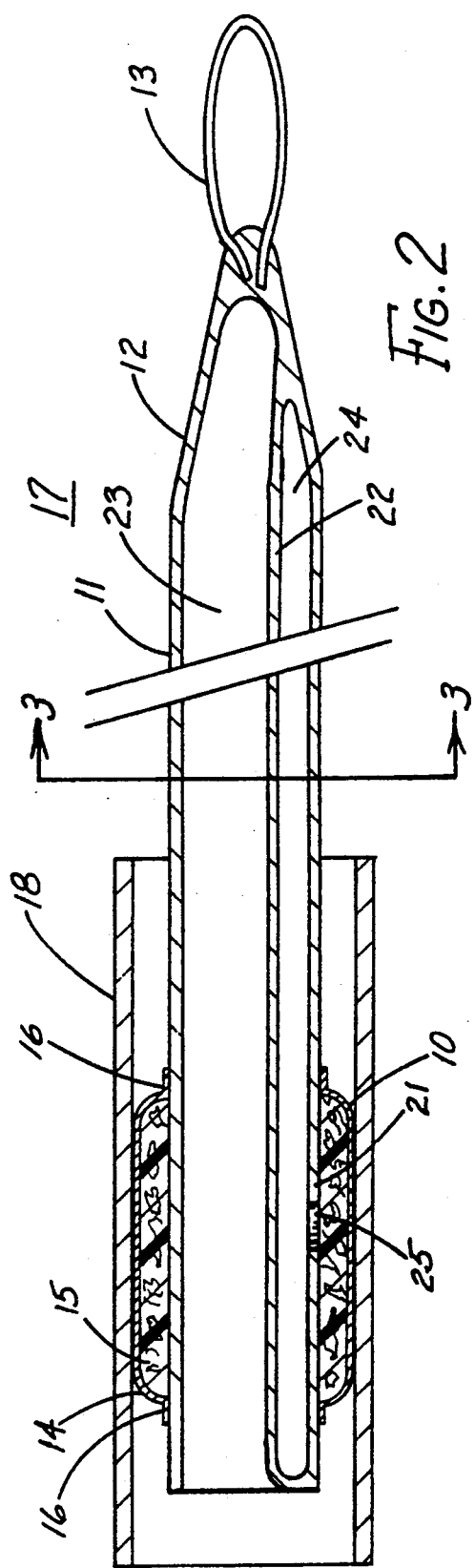

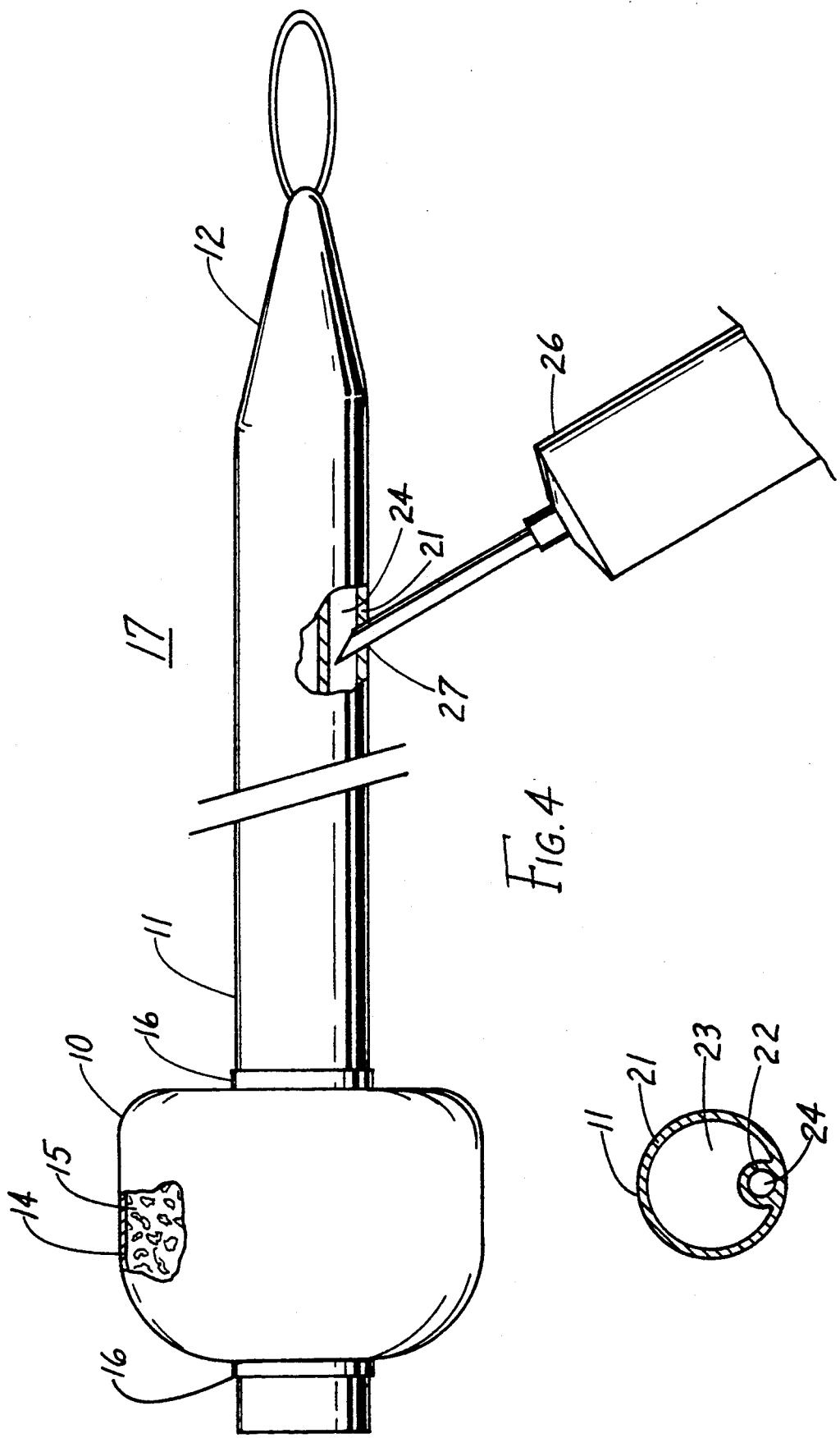

METHOD AND DEVICE FOR PERCUTANEOUS INTUBATION

BACKGROUND OF THE INVENTION

The present invention generally pertains to intubation devices and more specifically to a method and a device for intubating a stoma.

A percutaneous endoscopic technique is known, as described for example in U.S. Pat. No. 4,795,430, whereby an illuminating fiber optic endoscope is inserted into a patient's mouth and advanced into the stomach. The stomach is then inflated with air and the position of the endoscope may be externally visualized by the illuminating tip of the endoscope. The abdominal and gastric walls are then pierced at the position of the endoscope and a stoma thereby formed. In order to intubate the stoma, one end of a suture thread is passed externally through the stoma, snared by the endoscope and drawn upward through the stomach, esophagus and out the mouth of the patient. The suture is then tied to the end of a specially prepared catheter equipped with a length of suture to permit the catheter to be tied to the one end of the suture extending from the patient's mouth. The catheter is then intubated by pulling it in a retrograde manner through the mouth, esophagus, and into the stomach and through the stoma.

The catheter described in the above-mentioned U.S. Pat. No. 4,795,430 comprises a multi-lumen enteral feeding tube having a retention cuff near the distal end thereof which serves as a retention member to prevent the tube from exiting the stoma. The retention cuff, which is inflatable and deflatable through the inflation lumen of the tube, is substantially filled with a resilient sponge-like porous material for maintaining the cuff in fully inflated position. At the one end of the tube is an elongated tapered sleeve which encloses the one end of the tube and passes the suture loop therethrough for use in intubating the catheter. The sleeve includes a skirt portion which creates a seal about a side port of the tube which permits air to escape from the inflation lumen but prevents the ingress of air into the inflation lumen. Prior to intubating the catheter into a patient, the surgeon or gastroenterologist performing the procedure must squeeze the cuff to expel air out of the cuff through the inflation lumen. After the tube has been positioned in the patient, a portion of the proximal end of the tube, including the sleeve and skirt are cut off, exposing the inflation lumen to ambient air and allowing air to enter the retention cuff.

The sleeve device described in the prior art patent is intended to act as a one-way valve to allow the escape of air from the inflation lumen and to prevent the ingress of air into the inflation lumen. Typically, in order to obtain a more complete deflation of the cuff, a syringe is inserted in the inflation lumen to evacuate the cuff and the inflation lumen. Steps must then be taken to assure that the vacuum is retained when the syringe is removed from the inflation lumen. The skirt of the sleeve or another device is installed to seal the inflation lumen. Such evacuation steps are awkward and unnecessarily prolong the intubation procedure. This procedure may also lead to repeated cuff evacuation steps. Of particular concern is the unexpected inflation of the retention cuff while in the esophagus. As a result, the patient experiences unnecessary trauma and the possibility of an emergency surgical procedure. Thus, a specific problem of the prior art lies in the collapsing of the cuff just prior to intubation and keeping the cuff in the collapsed state during the intubation procedure.

SUMMARY OF THE INVENTION

These and other problems of the prior art are overcome in accordance with this invention by evacuating the retention cuff of an illustrative multi-lumen gastrostomy tube at a time prior to the intubation procedure, such as during manufacture or just prior to packaging rather than in the surgical suite, and applying an external retaining device to maintain the cuff in a collapsed state. The multi-lumen tube comprises a lumen for conveying fluids between a first and a second end of the tube and an inflation lumen having a port communicating with the cuff. The lumens are sealed at the one end of the tube. The sealed end is tapered and includes an attached device such as a loop of suture or atraumatic wire secured thereto for drawing the tube through the patient during the intubation procedure.

The cuff is filled with a resilient sponge-like material which has the property of maintaining a compressed shape for an ascertainable period of time after having been maintained in the compressed state for a predetermined time period. In one embodiment of the invention, the cuff is maintained in a collapsed state by means of a removable retaining sleeve. Advantageously, the retaining sleeve is applied when the cuff is compressed or collapsed at the time of manufacture or packaging of the tube. Just prior to insertion of the tube in the patient, the retaining sleeve is simply removed from the cuff without the necessity of taking the time during the procedure to collapse and evacuate the cuff. The cuff remains in the collapsed state during the procedure because the sponge-like material retains its compressed shape after having been maintained in the compressed state for a period of time prior to the intubation procedure. Upon completion of the intubation procedure, the tapered end piece of the tube is severed, opening the inflation lumen to ambient air, allowing for expansion of the cuff. The sponge-like material used in the cuff will preferably have the property that it has a very low rate of expansion in air and a faster rate of expansion in a liquid. To enhance expansion of the cuff after intubation, sterilized water is injected via the inflation lumen into the cuff, causing more rapid expansion of the sponge-like material.

It is a further advantage of this invention that the tube may be sealed in manufacture without requiring a specially designed sleeve having a skirt portion to prevent ingress of air as taught by the prior art.

BRIEF DESCRIPTION OF THE DRAWING

The invention may be better understood from the following detailed description when read with reference to the drawings in which:

FIG. 1 is a perspective view of a preferred embodiment of the invention;

FIG. 2 is a longitudinal section taken along line 2—2 in FIG. 1;

FIG. 3 is a vertical cross section taken along line 3—3 of FIG. 2; and

FIG. 4 is a perspective view of the device of FIG. 1 with an expanded cuff.

DETAILED DESCRIPTION

FIG. 1 shows a catheter 17 representing an illustrative embodiment of the present invention and comprising a multi-lumen enteral feeding tube 11 which may be intubated in a stoma by way of a known intubation technique. By that technique, a suture thread is drawn through a stoma, the stomach and the esophagus to the patient's mouth. The catheter is then intubated by attaching it to the suture and drawing the catheter in a retrograde manner through the mouth, the esophagus and the stomach until one end of the catheter extends beyond the stoma. The tube is provided with an inflatable expandable retention cuff 10 which acts to prevent the tube 11 from escaping through the stoma. The cuff 10 may be retained in its compressed state by means of a removable tubular sleeve 18, shown in cutaway section in FIG. 1. The sleeve 18 is removed prior to intubation. The cuff 10 has a distensible outer wall 14 and is filled with a resilient sponge-like foam material 15 which is allowed to expand when the cuff is inside the stomach. The tube is sealed at one end and preferably tapered to form an elongated conical terminal end 12 to facilitate parting of the esophageal and gastric tissues during the intubation procedure. Disposed on terminal end 12 and fixedly attached thereto is an attached device such as an atraumatic wire or suture loop 13 for attachment to a suture used in drawing the catheter 17 through the esophagus and stomach during the intubation procedure.

As shown in FIGS. 2 and 3, the tube 11 is provided with a delivery lumen 23 and an inflation lumen 24 separated by septum 22. The exterior wall 21 of inflation lumen 24 is provided with a port 25 communicating with the interior area of the cuff 10 to allow for the transfer of fluid between the cuff 10 and the inflation lumen 24.

FIG. 4 shows the cuff 10 in its expanded position. The cuff is filled with a sponge-like foam material 15 which preferably has a property that it will maintain a compressed state for an ascertainable period of time, e.g., approximately one hour, after having been maintained in the compressed state for a predetermined period of time, e.g., 24 hours. The foam material 15 preferably has the further property that it will expand relatively slowly in the presence of air and will expand much more rapidly in a liquid such as water. The latter property will facilitate expansion of the cuff after intubation. The foam material 15 may, for example, be a polyurethane foam. Cuffs containing such foam are available from suppliers such as the Bivonia Corporation of Gary, Ind. The foam material 15 is shaped in such a fashion that it will inflate or expand the cuff 10 when the foam material is in its expanded state. Typically, the tube 11 is manufactured and cut to desired length, and the walls of the cuff 10 are attached at points 16 of the tube 11, in a well-known manner, with the sponge-like material 15 in its expanded state contained within wall 14. The sponge-like material 15 will generally be in its expanded state when the cuff 10 is first attached to the tube. The cuff is attached in a region of the tube 11 which includes port 25 such that fluid can flow between the interior of the cuff 10 and the inflation lumen 24.

After the cuff has been attached in a well-known fashion, and preferably before the end 12 of the tube has been sealed, the cuff 10 is collapsed by a compression force on the outside surface of the cuff to expel air from inside the cuff through port 25 and inflation lumen 24 and to compress the sponge-like material. The cuff 10 may be collapsed after the end 12 has been sealed, for example, as part of the catheter packaging process. In that case, access to the inflation lumen 24 may be obtained by puncturing the exterior wall 21 of the tube 11 to provide a temporary port 27. After air has been expelled from the cuff, the port 27 may again be sealed. The temporary port 27 is preferably made in proximity of the end 12, since this end will be cut off and discarded after intubation. To aid in evacuating the cuff 10, a syringe such as depicted at 26 in FIG. 4 may be used.

When the cuff is in its collapsed state, the tubular sleeve 18 with longitudinal slit 19 is placed over cuff 10 and secured with tie 20 to maintain the cuff in its collapsed state. The purpose of the sleeve 18 is to retain the sponge-like material 15 in a tightly collapsed state over a period of time. The cuff outer wall 14 is preferably made of a thin silicon material. However, such material tends to be somewhat porous to air, which may allow the sponge-like material to expand over time. The sleeve 18 aids in collapsing the cuff and in retaining it in a tightly collapsed state. The interior diameter of the sleeve 18 is chosen to snugly fit over the cuff and such that frictional force between the outer wall of the cuff and inner wall of the sleeve will retain the sleeve in its desired position. Preferably, the cuff will be compressed to such an extent that the collapsed cuff will present as small a cross section as practical during the intubation process. The sleeve 18 is left in position on the cuff for a period of time, e.g., at least 24 hours, to hold the sponge-like material in its compressed state for that period of time. Prior to intubating the catheter into a patient, the sleeve 18 is removed from the cuff. The sponge material will retain its compressed state for at least a sufficient period of time to complete a normal intubation procedure, thereby minimizing the discomfort to the patient due to the presence of the cuff.

After intubation of the catheter, the conical end 12 will be present external to the patient's abdominal wall area and the cuff 10 will be positioned internal to the stomach. The conical end 12 is separated from the remainder of the tube by cutting the tube near the end 12 exposing the fluid lumen and the inflation lumen. The purpose of the cuff 10 is to prevent the tube 11 from escaping through the stoma. To expand the cuff, thereby presenting a larger retaining surface to the inside of the stomach wall, a liquid, e.g., sterilized water, is injected in the inflation lumen. The polyurethane foam material used in this application is of the preferred type which has the general property that it expands much more rapidly in the presence of a liquid such as water than in the presence of air. Accordingly, while the cuff is exposed to ambient air through the inflation lumen after the sealed end 12 has been cut off, the expansion of the foam in enhanced by the addition of the sterilized water. An amount of water sufficient to generally fill the cavity of the cuff 10 is added by means of a syringe via the inflation lumen 24, to more rapidly expand the cuff inside the body cavity. The inflation lumen is then self-sealed when the delivery lumen is capped.

It will be understood that the above-described embodiments are simply illustrative of the invention and that numerous other applications may be envisioned by those skilled in the art without significantly departing from the spirit of the invention.

What is claimed is:

1. An intubating device for intubating a stoma comprising:
   a multi-lumen tube;
   an inflatable retention cuff attached near one end of said tube and having a generally rounded configuration in an inflated state and a generally elongated configuration in a collapsed state;

said cuff comprising an outer wall and a sponge-like material contained by said outer wall, said sponge-like material having a compressed state and remaining in said compressed state for an ascertainable period of time after having been maintained in said compressed state for a predetermined period of time;

said tube comprising an inflation lumen having only a port communicating with said cuff to allow fluid flow to and from said cuff; and means positioned around said cuff for maintaining said cuff in said collapsed state for at least said predetermined period of time, wherein said means for maintaining is removed a period of time less than said ascertainable period of time prior to completion of intubation of said intubating device in a patient, said cuff remaining in said collapsed state during intubation and being expanded by the inflow of fluid in said cuff through said inflation lumen after intubation.

2. The device in accordance with claim 1, wherein said sponge-like material has a first rate of expansion in air and a second faster rate of expansion in a liquid, and wherein said cuff is expanded to said inflated state by the injection of said liquid in said inflation lumen after intubation of said device.

3. The intubating device in accordance with claim 2, wherein said sponge-like material comprises polyurethane foam.

4. The intubating device in accordance with claim 1, wherein said means for maintaining comprises a tubular sleeve surrounding said cuff.

5. An intubating device for intubating a stoma comprising:

a tube having a first end and a second end and at least a first lumen for conveying fluids between said first and said second ends and a second lumen;

an inflatable retention cuff attached near the second end of the tube and having a generally rounded configuration in an inflated state and a generally elongated configuration in a deflated state;

said second lumen having only a port communicating with said cuff to allow fluid flow to and from said cuff, said second lumen being sealed with said cuff in said deflated state;

a removable retaining device positioned around said cuff for maintaining said cuff in a collapsed state, wherein said removable retaining device is removed prior to completion of intubation of the intubating device in a patient and said second lumen is opened to allow inflation of said cuff after intubation.

6. The intubating device of claim 5 wherein said cuff comprises an outer wall and a resilient sponge-like material contained by the outer wall to aid in inflation of said cuff.

7. The intubating device in accordance with claim 6 wherein said resilient sponge-like material has the property that it will temporarily retain a compressed shape after removal of said retaining device.

8. The intubating device in accordance with claim 7 wherein said sponge-like material has the property that it expands in the presence of a liquid and wherein a liquid is injected in the cuff via said second lumen after injection.

9. The intubating device in accordance with claim 8, wherein said sponge-like material comprises a polyurethane foam.

10. The intubating device of claim 5 wherein said retaining device comprises a tubular sleeve.

11. An intubating device in accordance with claim 5 wherein said first end has a conically-shaped, sealed end comprising an attached device for drawing said intubating device through a stoma.

12. A method for intubating a stoma formed by percutaneous endoscopic technique including passing one end of suture externally through the stoma to the patient's mouth, another end of the suture remaining outside the stoma, and further comprising the steps of:

tying the suture to one end of a tube having an inflatable cuff near another end of said tube and having a removable sleeve for maintaining said cuff in a compressed state, said tube further comprising a first lumen extending from said one end to said other end and a second lumen extending from said one end and communicating with said inflatable cuff, said second lumen being sealed therealong for also maintaining said cuff in said compressed state;

removing said removable sleeve;

pulling said other end of said suture to draw said one end of said tube in a retrograde manner through said stoma; and opening said secondary lumen to inflate said cuff.

13. The method in accordance with claim 12 and further comprising the steps of:

compressing said cuff and applying said sleeve over said cuff and sealing said second lumen at said one end.

14. The method in accordance with claim 13 and further comprising the step of evacuating the said cuff in the compressed state prior to said step of sealing said second lumen.

15. The method in accordance with claim 12 and further comprising the step of injecting sterilized water in said second lumen after said step of opening said second lumen to inflate said cuff.

* * * * *